(12) United States Patent
Hasei et al.

(10) Patent No.: US 6,319,377 B1
(45) Date of Patent: Nov. 20, 2001

(54) NITROGEN OXIDE SENSOR

(75) Inventors: Masaharu Hasei; Yongtie Yan; Yunzhi Gao; Takashi Ono; Akira Kunimoto, all of Kumagaya (JP)

(73) Assignee: Kabushiki Kaisha Riken, Tokyo (JP)

(*) Notice: Subject to any disclaimer, the term of this patent is extended or adjusted under 35 U.S.C. 154(b) by 0 days.

(21) Appl. No.: 09/191,109

(22) Filed: Nov. 13, 1998

(30) Foreign Application Priority Data

Nov. 14, 1997 (JP) .................................................. 9-329637
Aug. 20, 1998 (JP) ................................................ 10-234337

(51) Int. Cl.[7] .................................................. G01N 27/407
(52) U.S. Cl. ........................ 204/425; 204/426; 204/427; 204/421; 204/293
(58) Field of Search .............................. 204/293, 421–429

(56) References Cited

U.S. PATENT DOCUMENTS

| | | | |
|---|---|---|---|
| 3,843,400 | * | 10/1974 | Radford et al. ........................ 204/421 |
| 4,021,326 | * | 5/1977 | Pollner et al. ........................ 204/429 |
| 4,502,939 | * | 3/1985 | Holfelder et al. .................... 204/426 |
| 4,927,517 | * | 5/1990 | Mizutani et al. ..................... 204/425 |
| 5,672,811 | * | 9/1997 | Kato et al. ............................ 204/426 |
| 5,861,092 | * | 1/1999 | Kiyota et al. ......................... 204/425 |

FOREIGN PATENT DOCUMENTS

| | | |
|---|---|---|
| 4-142455 A | 5/1992 | (JP) . |
| 6-123726 A | 5/1994 | (JP) . |
| 6-160324 A | 6/1994 | (JP) . |
| 6-194605 A | 7/1994 | (JP) . |
| 6-216698 A | 8/1994 | (JP) . |
| 6-216699 A | 8/1994 | (JP) . |
| 8-271476 A | 10/1996 | (JP) . |

OTHER PUBLICATIONS

N. Kato et al; "Thick Film ZrO2 NOx Sensor"; Sae Technical Papers; 960334 (1996), Month unavailable, pp. 137–142.

* cited by examiner

*Primary Examiner*—T. Tung
(74) *Attorney, Agent, or Firm*—Kubovcik & Kubovcik

(57) ABSTRACT

A nitrogen oxide sensor enabled to enhance the measurement concentration of a total of nitrogen oxides by oxidizing or reducing the nitrogen oxides on the surfaces of electrodes in addition to the control of an oxygen concentration by an oxygen pump. An electrode (3a) in a gas chamber (18) constructing an oxygen pumping portion (3) is made of a material (e.g., Pt-3 wt % Rh) having a function to oxidize a nitrogen oxide gas.

10 Claims, 14 Drawing Sheets

NITROGEN OXIDE SENSOR

BACKGROUND OF THE INVENTION

1. Field of the Invention

The present invention relates to a nitrogen oxide sensor for detecting a concentration of a nitrogen oxide. More particularly, the invention relates to a nitrogen oxide device for converting NO into $NO_2$ or $NO_2$ into NO electrochemically.

2. Prior Art

A solid element type of nitrogen oxide sensor has been representatively disclosed in the Japanese Patent Laid-Open Publication No. Hei 4-142455 (1983). This sensor is equipped on an ion conductor with a nitrate electrode and a reference electrode to measure an electromotive force to be generated between the electrodes, so that it has sensitivity to NO and $NO_2$. Since the sensitivities of the electrodes to NO and $NO_2$ are different, however, the NOx concentration cannot be detected in an environment to be measured where the two gases (NO and $NO_2$) coexist, or the concentration of neither NO nor $NO_2$ can be detected.

In order to improve the sensitivities to NO and $NO_2$, there has been proposed (in the Japanese Patent Laid-Open Publication No. Hei 6-123726(1995)) an electromotive type sensor in which an oxide catalyzer of NO is applied to or mixed with an auxiliary electrode. According to this method, the NO gas in the coexisting gas of NO and $NO_2$ can be oxidized into a single gas of $NO_2$ so that the NOx concentration can be detected. Like the analyzing method of the prior art, however, the accuracy is decided by the oxidizing ability of the catalyst so that the NOx concentration is different from the actual value. Moreover, these sensors are troubled by their moisture and heat resistances because they employ a nitrate in the auxiliary electrode, so that they are substantially difficult for the practical purposes from the standpoint of long-term stability.

On the other hand, there has also been reported a sensor for measuring a change in the electric conductivity, as based on the NOx concentration, by making use of semiconductor characteristics of various oxides. In the Japanese Patent Laid-Open Publication No. Hei 6-160324 (1995), for example, there has been proposed a sensor using tin oxides as a gas sensitive member. However, this sensor is also different in the sensitivity to NO and $NO_2$ so that it cannot detect the NOx concentration in an environment to be measured where the two gases coexist.

In recent years, there has been proposed (in SAE TECHNICAL PAPER 960334 or the Japanese Patent Laid-Open Publication No. Hei 8-271476 (1997)) a method for electrolyzing NOx to detect the NOx concentration from the electrolytic current value. The detection principle itself of this sensor is developed from the electrolytic current type sensor which has been widely applied in the prior art to other gases. Specifically, an ion conductor is provided with two chambers, the first one of which lowers the oxygen concentration in the environment to be measured substantially to zero and reduces $NO_2$ to NO by an oxygen pump and the second one of which is equipped with electrodes for ionizing the oxygen produced from the reduced NO in the measured environment by applying a voltage to the electrodes thereby to detect the NOx concentration. The NOx concentration to be detected by the sensor highly depends on the performance of the oxygen pump. When the concentration of the gas to be detected is low, the interference of the residual oxygen concentration in the measured environment is high, and the signal current is minute. In a noisy circumstance as in an automobile, the S/N ratio is so poor that the NOx concentration is difficult to detect accurately.

We have proposed a mixed potential type NOx sensor and have filed patent applications published as Japanese Patent Laid-Open Publication Nos. Hei 6-194605 (1995), Hei 6-216698 (1995) and Hei 6-216699 (1995). However, these constructions are excellent in sensitivity to NO or $NO_2$ but are troubled by the mutual interference of NO or $NO_2$ or by the interference of a reducing gas.

SUMMARY OF THE INVENTION

The gas responsive characteristics of the mixed potential type sensor to the nitrogen oxide gases, especially to NO and $NO_2$ have opposite sensitive outputs to the concentration thereby to establish the mutual interference in the environment where the two gases coexist. Since the oxygen concentration is controlled by the oxygen pump, it is difficult to make a conversion into the single NO gas or the single $NO_2$ gas, and the mutual interference cannot be sufficiently avoided. There is demanded the construction of a sensor which has a high sensitivity output of the NOx to be detected and a high concentration dependency so that it can detect not only the NOx concentration accurately even in the noisy circumstance of the automobile or the like but also the total of nitrogen oxides contained in the environment to be detected. Therefore, the invention has an object to satisfy that demand.

In the total nitrogen oxide sensor combining the nitrogen oxide converting device and the electromotive force type or mixed potential type nitrogen oxide sensor, moreover, a stable sensor output cannot be produced due to the deterioration in the converting ability in a nitrogen oxide converting electrode, and the nitrogen oxide conversion ability has to be further improved to measure a low concentration of the nitrogen oxide accurately.

The present invention has an object to provide a nitrogen oxide converting device which has a higher nitrogen oxide converting ability free from being deteriorated even when the power is ON, and a nitrogen oxide sensor which has a high and stable sensor output by combining the converting device with the electromotive force type or mixed potential type nitrogen oxide sensor.

A nitrogen oxide sensor of the present invention is constructed such that there are integrated an oxygen pump portion, which employs an ion conductive solid electrolyte body and which is equipped with at least one pair of electrodes for sucking or discharging an oxygen gas electrochemically, and a NOx gas detecting portion which is equipped with a detecting electrode and a counter electrode, which is also a reference electrode, for detecting a NOx gas, and such that one of the electrodes of the oxygen pumping portion and either the detecting electrode or the detecting electrode and the counter electrode of the NOx gas detecting portion are arranged in a gas chamber communicating with an environment to be detected, so that the NOx gas concentration is detected in terms of a potential difference between the detecting electrode and the counter electrode which is heated to a predetermined temperature range by a heating mechanism. With respect to the electrodes composing the oxygen pumping portion, at least the electrode, which is formed in the gas chamber having the detecting electrode arranged therein, is a NOx converting electrode having an electrolytic performance in which the electrolytic current for NOx is higher than that for oxygen within a predetermined applied voltage range, so that on the NOx converting electrode, mainly the nitrogen oxide gas in the detected atmosphere, especially, NO is oxidized into $NO_2$, or $NO_2$ is reduced into NO thereby to detect the total of the nitrogen oxide gas.

Here, the nitrogen peroxide gas (e.g., $N_2O_5$) over $NO_2$ raises no trouble because its direction of the sensor output in the system of the invention is identical to that of $NO_2$, that is, the direction in which the sensor output increases with the increase in the concentration. On the other hand, the electrolytic direction on the NOx converting electrode depends upon the material and quality of the detecting electrode. In the case of the detecting electrode exhibiting a higher sensitivity to $NO_2$ than to NO, more specifically, it is preferable to detect NOx by applying a voltage to the NOx converting electrode as a positive electrode to effect a conversion into $NO_2$. In the case of a detecting electrode exhibiting a higher sensitivity for NO than for $NO_2$, on the other hand, it is preferable to detect NOx by applying a voltage to the NOx converting electrode as a negative electrode to effect a conversion into NO.

A nitrogen oxide converting device according to the invention is constructed to comprise: a solid electrolyte substrate having an oxygen ion conductivity; and a nitrogen oxide converting electrode of platinum and ruthenium and a counter electrode of platinum formed on said solid electrolyte substrate. A voltage is applied to this device to suck or discharge oxygen to or from the converting electrode thereby to oxidize NO electrochemically into $NO_2$ or to reduce $NO_2$ into NO.

There is further provided a nitrogen oxide converting electrode of platinum and ruthenium, which is given a high activity to the nitrogen oxide and stable even when energized, by optimizing the composition and mode of the converting electrode and by adding a third element of precious metal.

DESCRIPTION OF THE PREFERRED EMBODIMENTS

Figure 1:
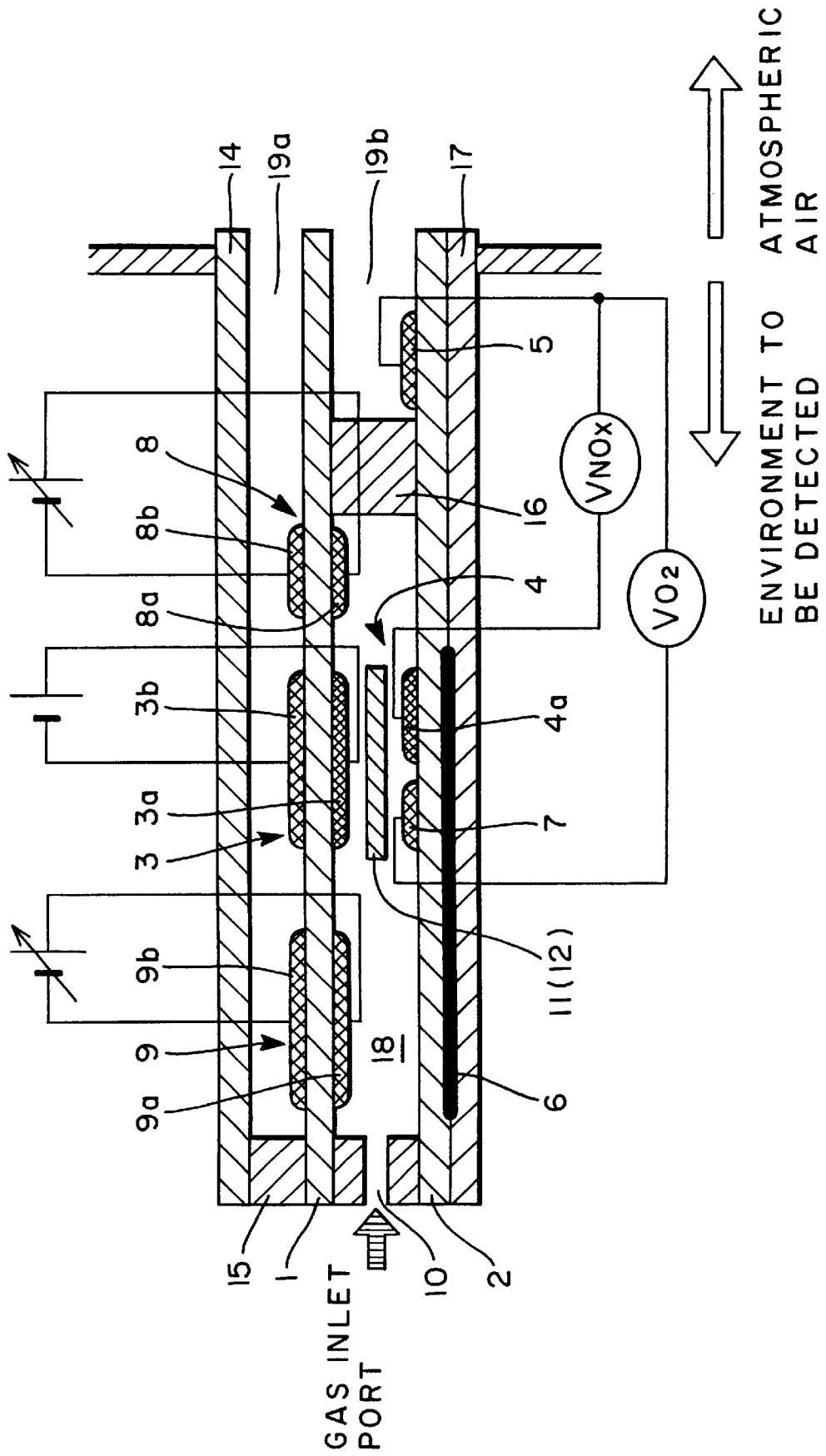
FIG. 1 is a schematic section showing a nitrogen oxide sensor according to the invention.
Figure 2:
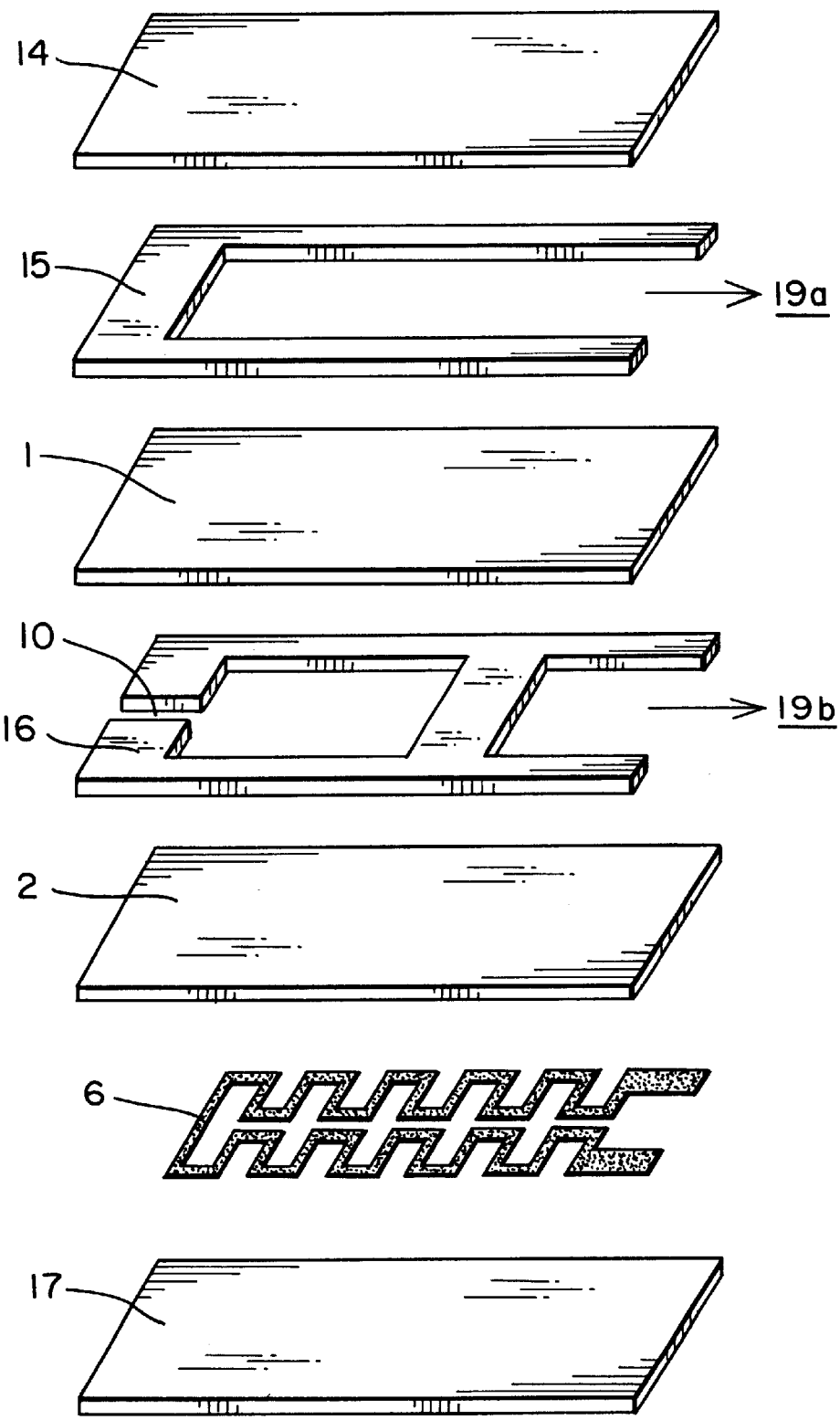
FIG. 2 is an exploded perspective view showing the nitrogen oxide sensor according to the invention.

FIGS. 1 and 2 show one embodiment of a nitrogen oxide sensor constructed of one gas chamber according to the invention. This construction will be described in detail by way of example.

A solid electrolyte body 1 or 2 is exemplified by a variety of solid electrolytes such as stabilized zirconia or partially stabilized zirconia and can employ any oxygen ion conductive material irrespective of a stabilizing agent and its amount of addition. The solid electrolyte 1 constructing an oxygen pumping portion 3 is molded into a plate shape and is equipped on its two faces with a NOx converting electrode 3a and a pumping electrode 3b so that it is activated as an oxygen pump by applying a predetermined voltage between the two electrodes 3a and 3b. When a voltage is applied to the NOx converting electrode 3a in a positive polarity and to the pumping electrode 3b in a negative polarity, the oxygen pumping portion 3 is driven to pump-in or supply such oxygen from an ambient duct 19a into a gas chamber 18. These electrodes 3a and 3b are prepared by forming a paste for the electrode material by a filling method such as a silk screening method and subsequently by baking the paste at a predetermined temperature. More preferably, the electrodes are made fine and given more active points participating in the pumping action by the sputter filming method. Of the electrodes 3a and 3b, at least the NOx converting electrode 3a to be arranged in the gas chamber 18 is made of a material exhibiting a higher electrolytic current value to the NOx gas than the oxygen within a predetermined electrolytic voltage range and is more preferably exemplified by a material having a high catalytic activity to NOx. This electrode material is effectively specified by an alloy or composite containing at least one of the elements including platinum, rhodium, iridium, palladium, ruthenium, gold, silver, chromium, nickel, manganese, iron, copper, tungsten, zinc and tin. The NOx converting electrode is exemplified preferably by an alloy or composite of Pt-(1–20 wt %) Rh and more preferably by an alloy of Pt-3 wt % Rh.

A NOx gas detecting portion 4 is constructed of the solid electrolyte body 2, a detecting electrode 4a and a counter electrode 5. At least the detecting electrode 4a is formed in the gas chamber 18 in which the electrode 3a of the oxygen pumping portion is arranged. The counter electrode 5 may also be arranged like the detecting electrode 4a in the gas chamber 18. When the counter electrode 5 has a significant activity on NOx, however, it exerts an influence upon the signal which is detected by the detecting electrode and based on the NOx concentration. Thus, the counter electrode 5 is preferably mounted in an ambient duct portion 19b vented to the atmospheric air or the reference atmosphere. Alternatively, the detecting electrode 4a and/or the counter electrode 5 may be formed on the solid electrolyte 1 constructing the oxygen pumping portion 3. The detecting electrode 4a is not especially limited, if it is made of an electrode material or has a mode active to NOx, and is prepared by forming a paste of an electrode material by the filming method or the screen printing method and subsequently by baking the paste at a predetermined temperature. More preferably, the detecting electrode 4a is an electrode which is made fine and given more active points participating into the response to NOx by the sputter filming method or the like.

The NOx gas concentration can be detected accurately if the oxygen concentration in the gas chamber 18, near the NOx detecting portion 4 is within a range of 0.01 to 10%. If the oxygen concentration is less than 0.1%, however, the speed of response is lowered. If the oxygen concentration is more than 5%, on the contrary, the speed of response is rather lowered with the reduction in the NOx sensitivity. The sensor to be mounted on a portion which is required to have a high response speed is preferred to have an oxygen concentration within a range of 0.1 to 5%. In the case of an automobile, the combustion state, i.e., the oxygen concentration existing in the exhaust gas atmosphere ranges widely according to the A/F ratio, and it is preferred to activate an auxiliary oxygen pumping portion 8 for setting the oxygen concentration in the NOx gas detecting portion 4 nor the gas chamber 18 within a range of 0.01 to 10%. The auxiliary oxygen pumping portion 8 may be constructed in at least either the solid electrolyte body 2 or the solid electrolyte body having the NOx gas detecting electrode 4a. The auxiliary oxygen pumping portion 8 is equipped, in at least either the solid electrolyte body 1 or 2 of the molded plate shape, with an electrode 8a arranged inside of the gas chamber 18 and an electrode 8b arranged outside of the same, so that it may be activated as an oxygen pump by applying a voltage between the two electrodes 8a and 8b. When the oxygen concentration in the gas chamber 18 is lower than a predetermined concentration range, more specifically, the auxiliary oxygen pumping portion 8 is operated to pump in or charge oxygen into the gas chamber from the electrode 8b placed outside of the gas chamber 18 communicating to the atmospheric air. When the oxygen concentration in the gas chamber 18 is higher than the predetermined concentration range, on the other hand, the oxygen pump is activated to pump-out or discharge the oxygen from the electrode 8a inside the gas chamber 18. These electrodes 8a and 8b are prepared by forming a paste of an electrode material by the filming method or the screen printing method and subsequently by baking the paste at a predetermined temperature. More preferably, the electrodes 8a and 8b are electrodes which are made fine and given more active points participating into the response to NOx by the sputter filming method or the like. The electrode 8a, as arranged inside of the gas chamber 18, is preferred to have no participation into the conversion of NOx but can be sufficiently used even if it has a far lower NOx gas conversion performance than that of the NOx converting electrode 3a or if it is operated under such drive conditions.

The NOx gas detection can be made more accurate if an oxygen concentration measuring portion is added to the NOx gas detecting portion 4 or the oxygen pumping portions 3 and 8 for controlling the oxygen concentration in the gas chamber 18. In the portion inside of the gas chamber 18 in the vicinity of the NOx gas detecting portion 4, more specifically, there is formed in the solid electrolyte body 1 or 2 an electrode 7 for detecting the oxygen concentration so that the oxygen concentration is measured in terms of a potential difference between the counter electrode 5 of the NOx gas detecting portion and the electrode 7. Here, the counter electrode 5 is more preferably disposed in the ambient duct portion 19b vented to the atmospheric air or the reference atmosphere. By controlling the drive voltage of the auxiliary oxygen pumping portion 8 with the oxygen concentration which is measured by the oxygen sensor portion, the oxygen concentration in the gas chamber 18 can be controlled to detect the NOx gas concentration accurately. The oxygen concentration detecting electrode 7 is prepared by forming a paste of the electrode material by the filming method such as the screen printing method and subsequently by baking the paste at a predetermined temperature.

In the construction of the invention, there are performed the actions to convert NO in the nitrogen oxide gas into $NO_2$, the nitrogen peroxide gas over $NO_2$ and their mixed gas on the NOx converting electrode 3a, as arranged inside of the gas chamber 18 of the oxygen pumping portion 3, the actions to convert $NO_2$ into NO, or the actions to measure the potential difference through the solid electrolyte body in the NOx gas detecting portion 4. In order to ensure these actions, the operating temperature is so important that the oxygen pumping portion 3 and the NOx gas detecting portion 4a have to be controlled to a temperature range of 400 to 750° C. by a heating mechanism. At a low temperature of lower than 400° C., specifically, the ion conductivity of the solid electrolyte body itself is so poor as to make it difficult to detect a stable output.

At a high temperature of higher than 750° C., on the other hand, NO is so difficult to oxidize that the measurements intended by the invention cannot be achieved. As a result, at least the NOx gas detecting portion has to be kept within the aforementioned temperature range or more preferably within a temperature range of 500 to 700° C. As the heating mechanism, there is adopted means which is used by adhering a plate heater 6 having a buried stable platinum heater either to the solid electrolyte body 2 having the oxygen pumping portion or the NOx gas detecting portion or to a partition 15 of an ambient duct 19. It is natural that the heater 6 may be so arranged on the two faces as to control the temperatures of the oxygen pumping portion and the NOx gas detecting portion separately, and that the temperature control may be suitably exemplified by either the feedback control according to the electric resistance of the heater itself or the feedback control using a separate temperature sensor such as a thermocouple.

The gas in the environment to be detected is introduced from a gas inlet port 10 into the gas chamber 18. Considering the long-term stabilities of the NOx converting electrode 3a and the pumping electrode 3b constructing the oxygen pumping portion 3 and the solid electrolyte body making the two electrodes, the voltage to be applied thereto is desired to be 1.5 V or lower, and the gas inlet port 10 is required to have such a gas diffusion resistance as to convert NOx at the applied voltage of 1.5 V or lower. In the case of the auxiliary oxygen pumping portion 8 for setting the oxygen concentration in the gas chamber 18 to 0.01 to 10%, it is necessary that the voltage to be applied to the auxiliary oxygen pumping portion 8 is 1.5 V or lower, and that the gas inlet port 10 has such a gas diffusion resistance as to control the oxygen concentration.

When NO is to be converted in the oxygen pumping portion 3 into $NO_2$, a nitrogen peroxide gas over $NO_2$ or their mixed gas, an oxidizing catalyzer 11 is so effectively formed in the gas chamber 18 as to prevent the converted gas from being reduced again into NO. When $NO_2$ is converted in the oxygen pumping portion 3 into NO, a reducing catalyzer 11 is so effectively formed in the gas chamber 18 as to prevent the converted gas from being oxidized again into $NO_2$.

When the NOx converting electrode 3a of the oxygen pumping portion and at least the detecting electrode 4a composing the NOx gas detecting portion are opposed to each other, a porous member 12 is interposed between the NOx converting electrode 3a and at least the detecting electrode 4a to reduce the spacing between the two electrodes so that NOx, as converted by the oxygen pumping portion 3, can be instantly detected by the NOx gas detecting portion. This porous member 12 can be more effective if it acts as the aforementioned oxidizing catalyzer or reducing catalyzer. When the porous member 12 is made of a material having an electrically high insulation, moreover, the NOx gas detecting portion can output a signal output without being influenced by the voltage for driving the oxygen pumping portion 3. Even when the porous member has an electronic conductivity, however, no problem arises if the circuit making the oxygen pumping portion and the circuit making the NOx gas detecting portion are absolutely different.

Figure 3:
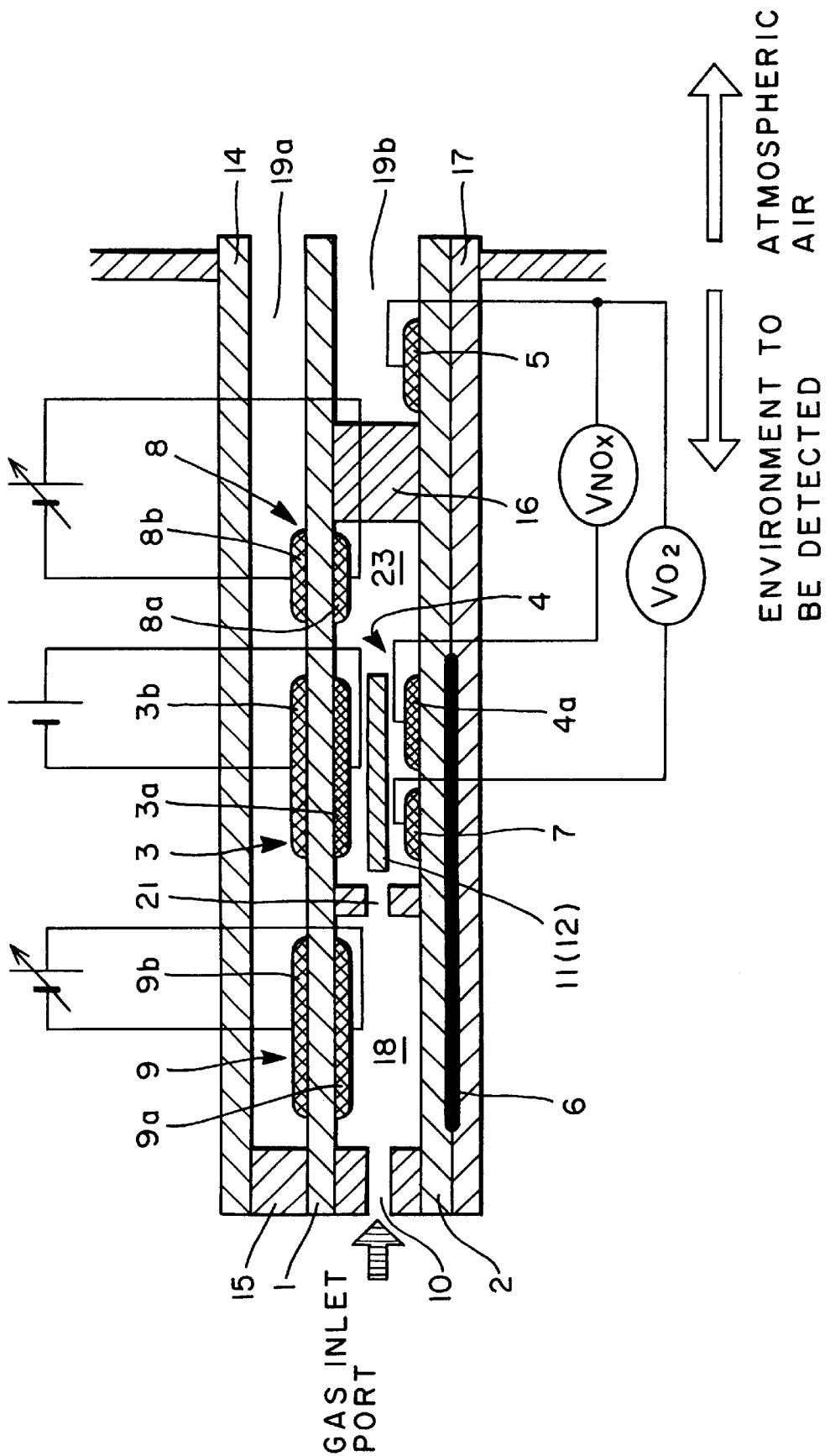
FIG. 3 is a schematic section showing a nitrogen oxide sensor, as constructed of two gas chambers, according to the invention.
Figure 4:
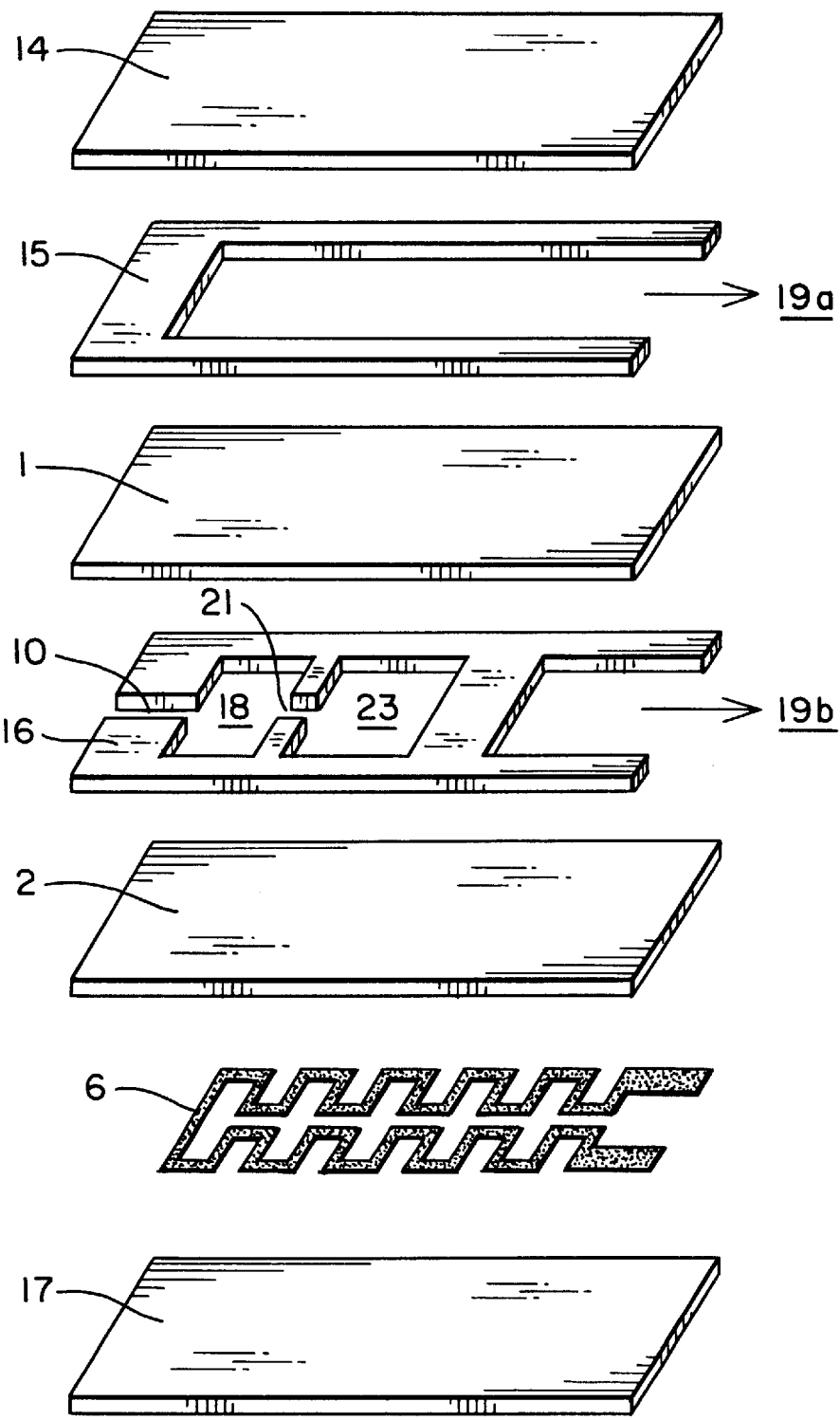
FIG. 4 is an exploded perspective view showing the nitrogen oxide sensor constructed of the two gas chambers according to the invention.

In order to oxidize a reduction inhibiting gas such as a hydrocarbon gas or CO gas sufficiently into a harmless gas, it is effective to provide a preliminary oxygen pumping portion 9 upstream of at least the detecting electrode. This preliminary oxygen pumping portion 9 may be mounted on at least either the solid electrolyte body 1 or the solid electrolyte body 2 having the detecting electrode 4a. The preliminary oxygen pumping portion 9 is equipped with an electrode 9a, which is arranged in the gas chamber 18 and on one of at least one of the plate-molded solid electrolyte bodies 1 and 2, and an electrode 9b arranged in the ambient duct 19a so that the oxygen pumping portion 9 is made to act as an oxygen pump by applying a voltage between the two electrodes 9a and 9b. If the gas chamber 18 has no oxygen necessary for oxidizing the reducing gas, moreover, the preliminary oxygen pumping portion 9 is made to act as an oxygen pump for sucking or pumping-in the oxygen into the gas chamber 18. There is no restriction on the material of the electrodes 9a and 9b if this material can perform an electrochemical pumping action. The electrodes 9a and 9b can be prepared by making a paste of the electrode material by a filming method such as the screen printing method and subsequently by baking the paste at a predetermined temperature. These electrodes may preferably be made fine to have increased active points participating in the pumping action by the sputter filming method. Moreover, it becomes more feasible to suppress the interference of the reduction interfering gas by making two gas chambers, as shown in FIGS. 3 and 4, and by mounting the preliminary oxygen pumping portion 9 in the first gas chamber 18 in the vicinity of the gas inlet port 10.

In any of the constructions, as detailed with reference to FIGS. 1 to 3, the output signal of the oxygen sensor portion, arranged in the gas chamber, is employed to correct the output signal of the NOx gas detecting portion thereby to detect it as the electromotive value of NOx so that the influence of the coexisting oxygen concentration can be suppressed to enhance the detection accuracy of the nitrogen oxide gas. When the detecting electrode 4a induces an electrochemical reaction between oxygen and NOx to establish a mixed potential, on the other hand, the detecting electrode 4a and the counter electrode 5 are formed in the common gas chamber so that the influence of the coexisting concentration is hardly received to enhance the detection accuracy of the nitrogen oxide gas and to make it unnecessary to form the ambient duct portion separately for the counter electrode.

Figure 5:
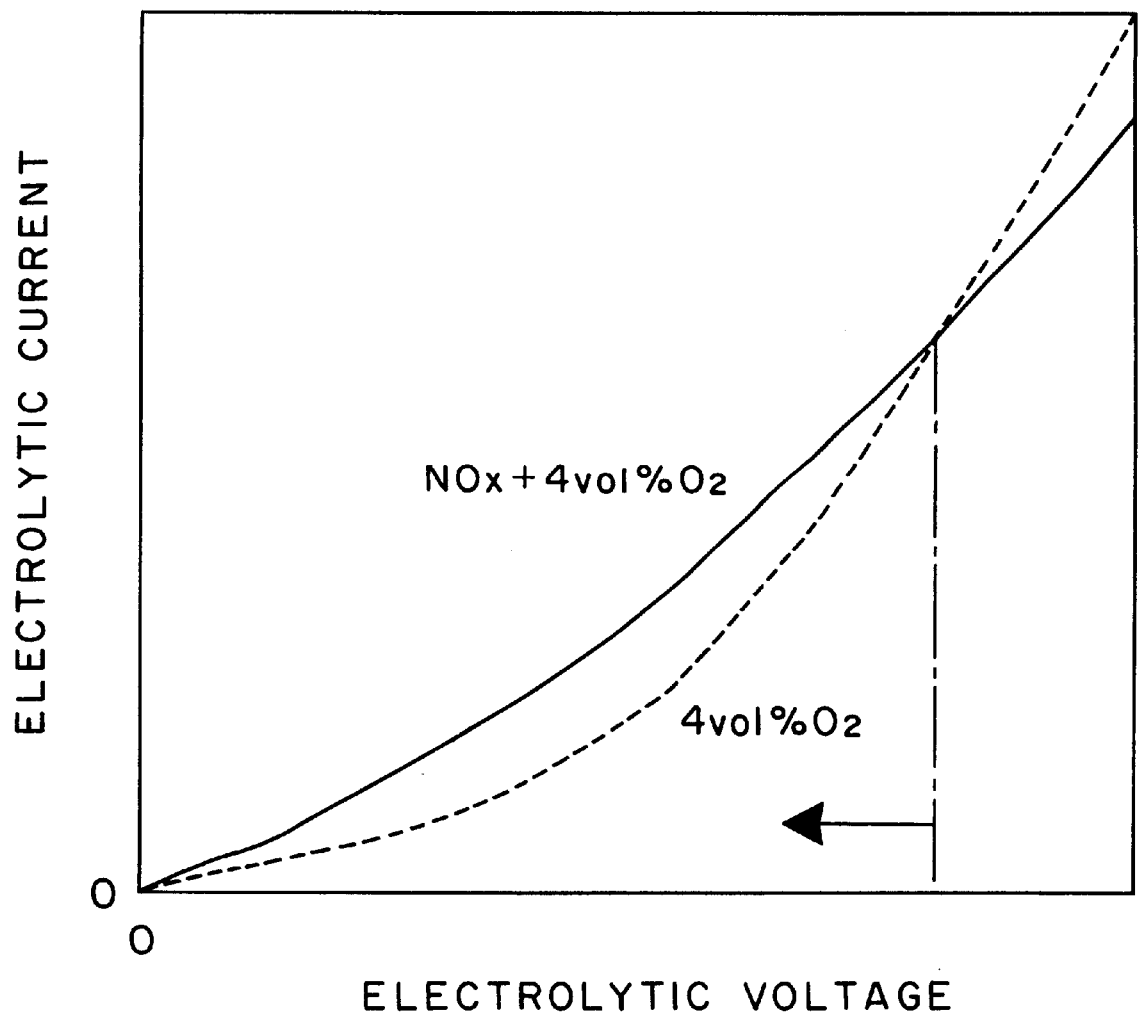
FIG. 5 is a graph schematically plotting one example of the relation between an electrolytic voltage and an electrolytic current in an oxygen atmosphere or in an atmosphere where oxygen and NOx coexist.

FIG. 5 schematically plots one example of the relation between an applied voltage between the two electrodes and an electrolytic voltage when a pair of platinum electrodes are formed on the solid electrolyte body to change the environment to be measured. By setting the applied voltage in the region where the electrolytic current value in the atmosphere containing NOx such as NO or $NO_2$ is higher than that in the atmosphere of oxygen only, the conversion of NOx on the oxygen pumping electrode such as the oxidation of NO to $NO_2$ is facilitated to occur. These characteristics vary depending upon the electrode material or the electrode mode, and it is preferred to form the NOx converting electrode of such an electrode material as will enlarge the difference between the electrolytic current value of oxygen in a predetermined electrolytic voltage and the electrolytic current voltage of NOx.

Figure 6:
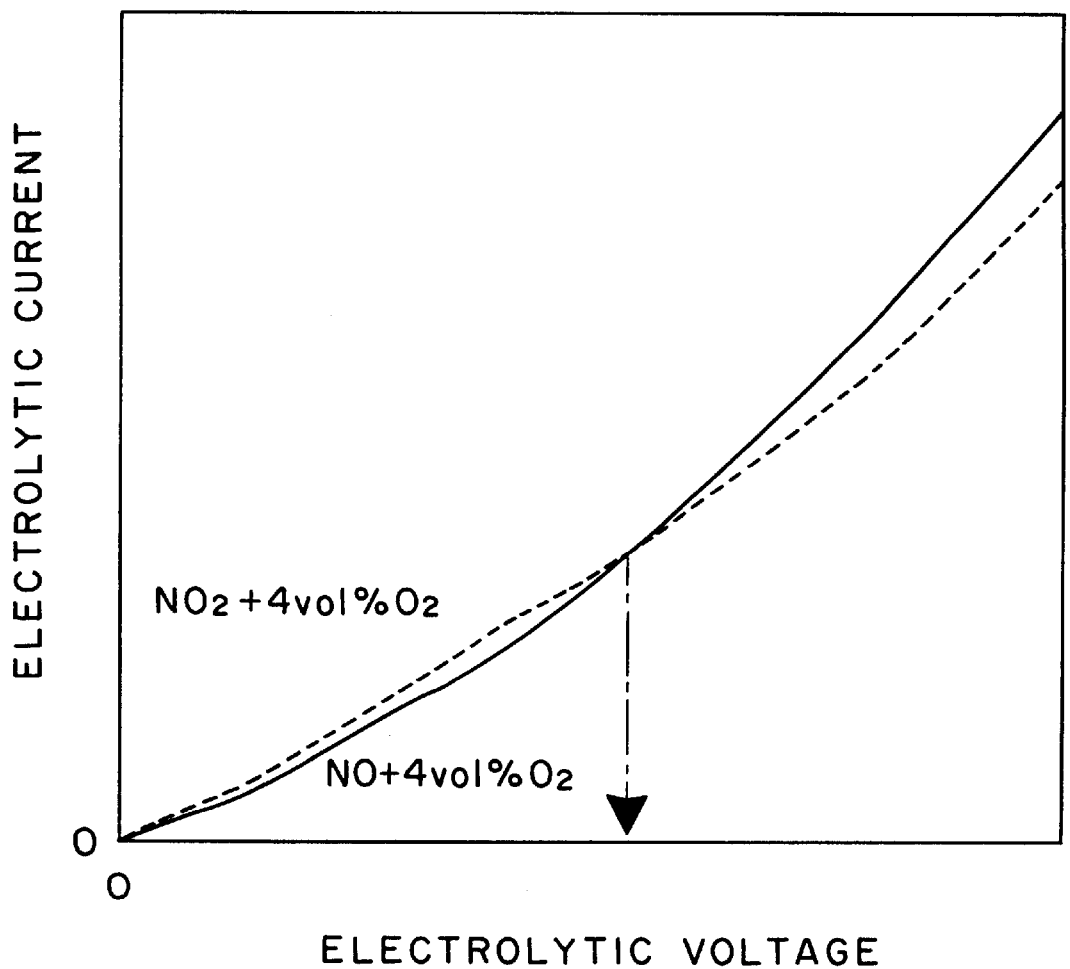
FIG. 6 is a graph schematically illustrating one example of the relation between an electrolytic voltage and an electrolytic current in an atmosphere containing NO or in an atmosphere containing $NO_2$.

FIG. 6 schematically plots one example of the relation between an applied voltage between the two electrodes and an electrolytic current when the NOx in the ambient to be measured is NO or $NO_2$. By driving the oxygen pumping portion at an electrolytic voltage value at which the electrolytic current for NO and the electrolytic current for $NO_2$ are equal, no prior gas conversion of NO or $NO_2$ is caused even if the existence percentage of the nitrogen oxide gas in the environment to be measured changes, so that the total of the nitrogen oxide gas can be easily detected.

The nitrogen oxide is constructed to have a high sensitivity and an excellent stability by using the oxygen pump for pumping-in or pumping-out oxygen electrochemically, such that the mutual interference of nitrogen oxide gases is suppressed either by converting the nitrogen oxide gas in an environment to be detected, especially NO and $NO_2$ on the NOx oxygen pumping electrode, as arranged in the gas chamber, of the electrodes composing the oxygen pump into $NO_2$, a nitrogen peroxide gas over $NO_2$ and their mixed gases or by converting $NO_2$ into NO.

The invention will be specifically described in connection with its embodiments but should not be limited thereto. Here will be detailed the case in which the NO gas is converted into the $NO_2$ gas, the nitrogen peroxide gas over $NO_2$ and their mixed gases. In the case of converting $NO_2$ into NO, the total of NOx can be detected as the output of NO by inverting the voltage to be applied to the NOx converting electrode (into the discharge direction).

(Example 1)

In the construction of FIG. 1, the nitrogen oxide sensor, as constructed to include the oxygen pumping portion, the auxiliary oxygen pumping portion, the NOx gas detecting portion and the oxygen sensor portion, was made of the following materials by the following procedure. The oxygen pumping portion was made of a green sheet containing zirconia stabilized with 6 mol % yttria and molded and worked to 0.2t×6 w×80$^l$ mm, and its electrodes were formed by applying electrode pastes by the screen printing method to the portions in the gas chamber and in the ambient duct. The NOx converting electrode was made of "PT-3 wt % Rh", and the pumping electrode was made of Pt.

The NOx gas detecting portion was made of the green sheet having the same material and size as those of the oxygen pumping portion. The detecting electrode was formed by applying a composite oxide paste of $NiCr_2O_4$ by the screen printing method, and the counter electrode was formed by applying a Pt paste by the screen printing method. The counter electrode was formed at the portion in the ambient duct. Here, the $NiCr_2O_4$ composite oxide paste was obtained by pulverizing the $NiCr_2O_4$ powder, as prepared by the solid phase method, with a bowl mill and drying it, and subsequently by blending the powder with ethyl cellulose and a diluting agent.

The auxiliary oxygen pumping portion was constructed on the green sheet, on which the oxygen pumping portion had been constructed, and downstream of the oxygen pumping portion. Both the electrodes in the gas chamber and the electrodes in the ambient duct were formed by applying the Pt paste by the screen printing method. The oxygen sensor portion was constructed on the green sheet which had constructed the NOx gas detecting portion. The oxygen concentration detecting electrode in the gas chamber was formed by applying the Pt paste by the screen printing method. The counter electrode was shared with that of the NOx gas detecting portion.

The heater was formed of a Pt paste of high purity different from that of the electrodes by the screen printing method. An alumina printed layer of high purity was formed on the green sheet of the same material and size as those of the oxygen pumping portion and was printed thereon with a heater pattern, and an alumina printed layer of high purity was laid over the former one. The gas inlet port was given a size of 0.02 t×0.5 W×1 mm. A gas chamber partitioning green sheet constructing the gas chamber was given a thickness of 0.2 mm.

The green sheets thus having the individual electrode and the heater formed thereon were laminated and baked at 1,400° C. for 5 hours to produce a nitrogen oxide sensor in which the oxygen pumping portion, the NOx gas detecting portion and the heater were integrated.

The heater thus made was examined on its output by keeping it at 600° C. with the buried heater and by placing in the simulation gas having a known composition. The auxiliary oxygen pump was controlled to set the oxygen concentration in the gas chamber to 4%. The results are enumerated in Table 1. The sensor produced the outputs which were logarithmically proportional to the concentration of $(NO_2+NO)$ gas, and had a higher sensitivity than those of Comparisons, as had been proposed in the prior art to effect the NOx conversions by controlling the oxygen concentration.

TABLE 1

| Nos. | Test Gas Composition | | | Detector |
| --- | --- | --- | --- | --- |
| | NO (ppm) | $NO_2$ (ppm) | NO + $NO_2$ (ppm) | Output (mV) |
| 1 | 50 | 0 | 50 | 39 |
| 2 | 50 | 50 | 100 | 58 |
| 3 | 100 | 50 | 150 | 70 |
| 4 | 150 | 0 | 150 | 68 |
| 5 | 0 | 150 | 150 | 69 |
| Comp. 1 | 50 | 0 | 50 | 35 |
| Comp. 2 | 50 | 50 | 100 | 50 |
| Comp. 3 | 100 | 50 | 150 | 60 |

(Example 2)

In the construction, the nitrogen oxide sensor, as constructed to include the oxygen pumping portion, the auxiliary oxygen pumping portion, the preliminary oxygen pumping portion, the NOx gas detecting portion and the oxygen sensor portion, was made. The materials, qualities, sizes and baking conditions for making the individual portions other than the preliminary oxygen pumping portion were identical to those of Example 1. The preliminary oxygen pumping portion was formed on the green sheet, on which the oxygen pumping portion was made, and upstream of the oxygen pumping portion. Both the electrodes in the gas chamber and the electrodes in the ambient duct were formed by applying the Pt paste by the screen printing method.

The sensor thus made was examined on its outputs by keeping it at 600° C. with the buried heater and by placing it in the simulation gas having a known composition. The preliminary oxygen pumping portion was so driven with an applied voltage of 0.5 V as to suck oxygen into the gas chamber, and the auxiliary oxygen pump was so controlled as to set the oxygen concentration in the gas chamber to 4%. The results are enumerated in Table 2. The outputs are logarithmically proportional to the concentration of $(NO_2+NO)$ gas without being influenced by the concentrations of $C_3H_6$, CO and oxygen.

TABLE 2

| | Test Gas Composition | | | | | | | |
| --- | --- | --- | --- | --- | --- | --- | --- | --- |
| Nos. | NO (ppm) | $NO_2$ (ppm) | $O_2$ (%) | $C_3H_6$ (ppm) | CO (ppm) | $N_2$ | NO + $NO_2$ (ppm) | Output (mV) |
| 1 | 50 | 0 | 0.005 | 0 | 0 | bal. | 50 | 39 |
| 2 | 50 | 50 | 0.005 | 0 | 0 | bal. | 100 | 58 |
| 3 | 100 | 50 | 0.005 | 0 | 0 | bal. | 150 | 70 |
| 4 | 100 | 50 | 0.005 | 100 | 0 | bal. | 150 | 71 |
| 5 | 100 | 50 | 0.005 | 100 | 100 | bal. | 150 | 72 |
| 6 | 100 | 50 | 0.5 | 100 | 100 | bal. | 150 | 70 |
| 7 | 100 | 50 | 10 | 100 | 100 | bal. | 150 | 73 |

(Example 3)

In the construction of FIG. 1, the nitrogen oxide sensor, as constructed to include the oxygen pumping portion, the auxiliary oxygen pumping portion, the NOx gas detecting portion, the oxygen sensor portion and the porous member, was made. The gas chamber partitioning green sheet for constructing the gas chamber was given a thickness of 40 μm, and the oxygen pumping electrode and the NOx detecting electrode in the gas chamber were made to contact each other through a porous alumina film. Also made was a sensor in which the oxygen pumping electrode and the NOx detecting electrode in the gas chamber were in contact through a porous film containing alumina carrying palladium. The materials, qualities, sizes and baking conditions for making the oxygen pumping portion, the auxiliary oxygen pumping portion, the NOx gas detecting portion and the oxygen sensor portion were identical to those of Example 1. The counter electrode was formed in the ambient duct, and the counter electrode of the oxygen sensor was also shared.

Figure 7:
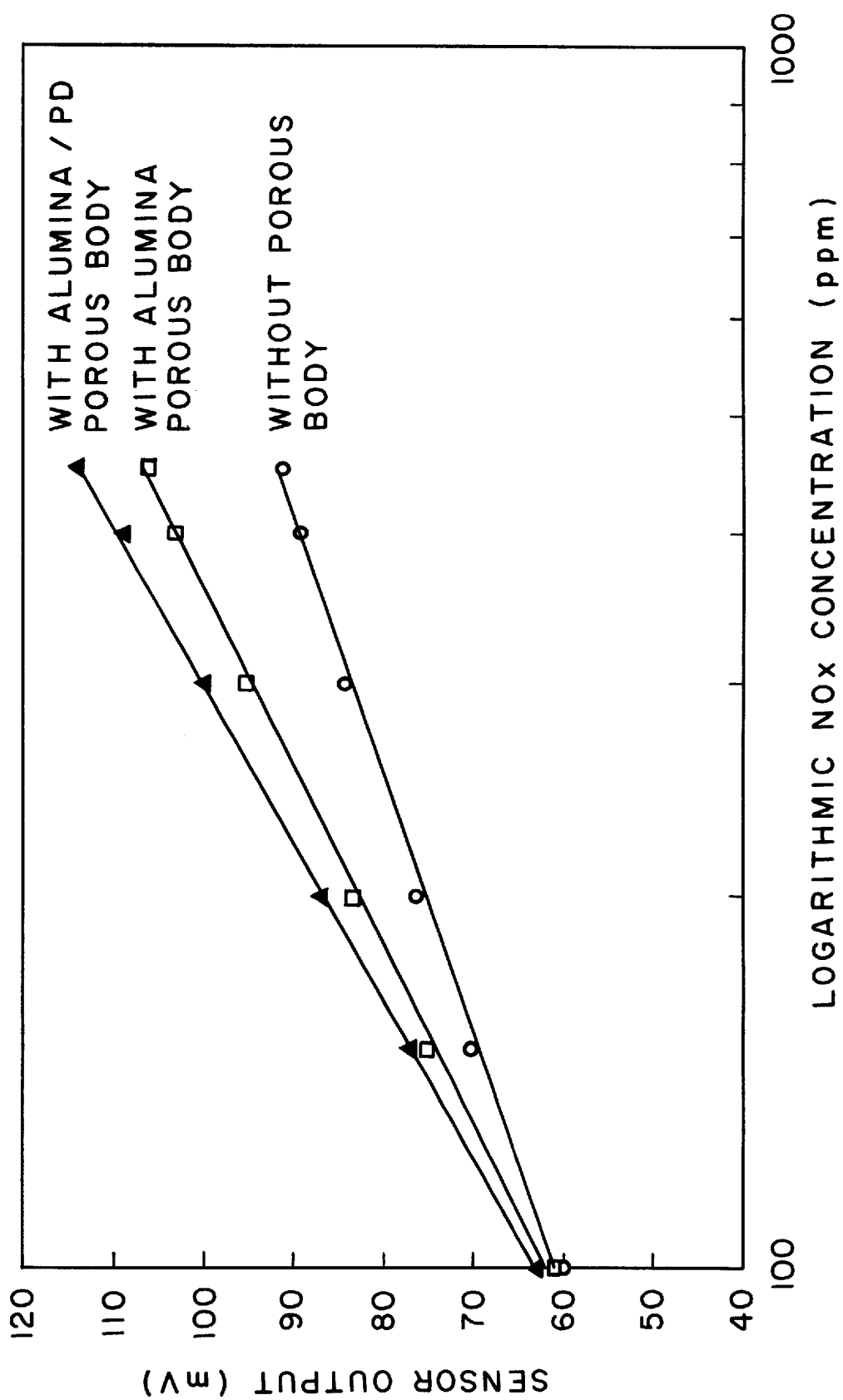
FIG. 7 is a graph illustrating the effects of porous members in the relations between the NOx concentration and the sensor outputs of the nitrogen oxide sensor, as constructed of one gas chamber, according to the invention.

The sensors thus made were examined on their outputs by keeping them at 600° C. with the buried heater and by placing them in NOx of 50 to 400 ppm NO+50 ppm $NO_2$. The auxiliary oxygen pump was controlled to set the oxygen concentration in the gas chamber to 4%. The results were plotted in FIG. 7. For comparisons, there are also plotted the result which was obtained by using the sensor of Example 1. The dependency of the sensor output on the NOx concentration is higher in case the oxygen pumping electrode and the NOx detecting electrode were in contact through the porous alumina film, than of the sensor of Example 1 having no porous member. The dependency of the sensor output on the NOx concentration becomes the higher in case the porous film contained alumina carrying palladium.

(Example 4)

In the construction of FIG. 1, the nitrogen oxide sensor, as constructed to include the oxygen pumping portion, the auxiliary oxygen pumping portion, the NOx gas detecting portion, the oxygen sensor portion and the porous member, was made. The gas chamber partitioning green sheet for constructing the gas chamber was given a thickness of 40 μm, and the oxygen pumping electrodes and the NOx detecting electrodes in the gas chamber were made to contact with each other through the porous alumina film. The materials, qualities, sizes and backing conditions for making the auxiliary oxygen pumping portion, the NOx gas detecting portion and the oxygen sensor portion were identical to those of Embodiment 1. The counter electrode was formed in the ambient duct, and the counter electrode of the oxygen sensor was shared. The oxygen pumping portion had the NOx converting electrode made of a material, as tabulated in Table 3, the pumping electrode made of platinum, and the size and baking conditions identical to those of Embodiment 1.

The sensor thus made was examined on its outputs by keeping it at 600° C. with the buried heater and by placing it in NOx of 100 ppm NO+50 ppm $NO_2$. The auxiliary oxygen pump was so controlled to set the oxygen concentration in the gas chamber to 4%. The results are tabulated in Table 3. Any of the oxygen pumps generated outputs of satisfactory NOx sensitivities to effect sufficient NOx gas conversions.

TABLE 3

| Nos. | NOx Converting Electrode | Test Gas Composition NO (ppm) | Test Gas Composition $NO_2$ (ppm) | NO + $NO_2$ (ppm) | Output (mV) |
|---|---|---|---|---|---|
| 1 | Pt | 100 | 50 | 150 | 60 |
| 2 | Pt-3 wt % Rh | 100 | 50 | 150 | 70 |
| 3 | Rh | 100 | 50 | 150 | 68 |
| 4 | Pt-5 wt % Ir | 100 | 50 | 150 | 66 |
| 5 | Ir | 100 | 50 | 150 | 63 |
| 6 | Pt-5 wt % Pd | 100 | 50 | 150 | 69 |

TABLE 3-continued

| Nos. | NOx Converting Electrode | Test Gas Composition NO (ppm) | Test Gas Composition $NO_2$ (ppm) | NO + $NO_2$ (ppm) | Output (mV) |
|---|---|---|---|---|---|
| 7 | Pd | 100 | 50 | 150 | 67 |
| 8 | Pt-5 wt % Ru | 100 | 50 | 150 | 63 |
| 9 | Pt-5 wt % Au | 100 | 50 | 150 | 62 |
| 10 | Pt-5 wt % Ag | 100 | 50 | 150 | 61 |
| 11 | Pt-5 wt % Cr | 100 | 50 | 150 | 65 |
| 12 | Pt-5 wt % Ni | 100 | 50 | 150 | 64 |
| 13 | Pt-5 wt % $NiCr_2O_4$ | 100 | 50 | 150 | 63 |
| 14 | Pt-5 wt % Mn | 100 | 50 | 150 | 66 |
| 15 | Pt-5 wt % Fe | 100 | 50 | 150 | 60 |
| 16 | Pt-5 wt % Cu | 100 | 50 | 150 | 62 |
| 17 | Pt-5 wt % W | 100 | 50 | 150 | 63 |
| 18 | Pt-5 wt % Zn | 100 | 50 | 150 | 62 |
| 19 | Pt-5 wt % Sn | 100 | 50 | 150 | 64 |

Figure 8:
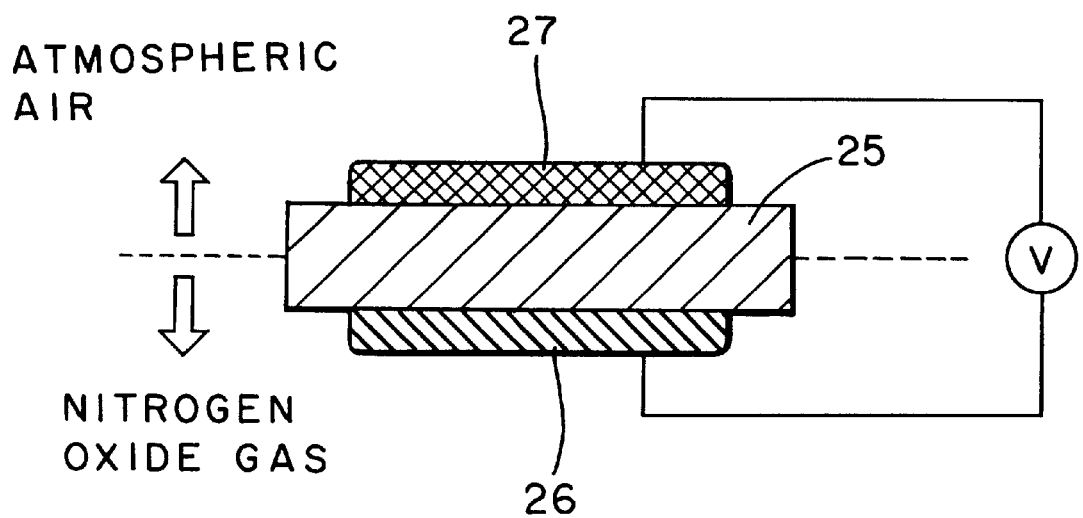
FIG. 8 is a schematic section showing a conversion device of the invention.

FIG. 8 shows one example of a nitrogen oxide converting device according to the invention. The invention will be detailed by way of this construction.

The oxygen ion conducting solid electrolyte body an be exemplified by an oxygen ion conductor 25 such as stabilized zirconia or partially stabilized zirconia, if it has an oxygen ion conductivity independent of a stabilizing agent or an amount of addition. However, it is preferable to employ a solid electrolyte body having high oxygen ion conductivity.

A nitrogen oxide converting electrode 26 is made of either a material of platinum and ruthenium exhibiting a high electrode reaction activity to a nitrogen oxide within a predetermined voltage range or a material containing platinum, ruthenium, a third metal element and an addition of fine powder of stabilizing zirconia. The precious metal powder is exemplified by a mixture or an alloy material but preferably by fine powder of an alloy. The nitrogen oxide converting electrode 26 of platinum and ruthenium is made of a composite of platinum and 0.1 to 20 wt % of ruthenium but, more preferably, an alloy material of platinum and 1 to 10 wt % of ruthenium.

The nitrogen oxide converting electrode 26 of platinum, ruthenium and a third element is exemplified by a composite of platinum, 1 to 5 wt % of ruthenium and 0.1 to 10 wt % of a third element but, more preferably, an alloy material of platinum, 3 to 5 wt % of ruthenium and 0.5 to 5 wt % of a third element. Here, this third element is one kind of rhodium, iridium, palladium, gold and silver.

In order to increase the active points, on the other hand, the nitrogen oxide converting electrode 26 is preferably exemplified by adding 5 to 15 wt % of stabilized zirconia to the converting electrode 26. The electrode film may fail to have an electric conductivity if the addition of stabilizing zirconia exceeds 15 wt %. The thickness of the nitrogen oxide converting electrode 26 is desired to be 3 to 30 μm but is preferred to be within a range of 5 to 15 μm.

A counter electrode 27 is made of a material of platinum having a high activity to oxygen or, more preferably, a material containing platinum and an addition of stabilized zirconia powder. In order to increase the active points of the electrode 27 to oxygen by increasing the three-phase interface of the gas, the electrode and the solid electrolyte body, it is preferable to employ fine powder of platinum and fine powder of stabilizing zirconia. On the other hand, the platinum counter electrode 27 is preferably exemplified by adding 5 to 15 wt % of stabilizing zirconia to the total weight of platinum and stabilizing zirconia. The counter electrode 27 is preferred to have a thickness within a range of 3 to 30 μm.

The nitrogen oxide converting electrode 26 and the platinum counter electrode 27 can be made by forming an electrode paste by a filming method such as the screen printing method and subsequently by baking the paste at a predetermined temperature.

The nitrogen oxide converting device having the construction shown in FIG. 8 is heated to a temperature range of 300 to 800° C. by applying a voltage of 0.1 to 1.0 V to suck or pump-in oxygen into the converting electrode 26 thereby to oxidize NO to $NO_2$, or to discharge or pump-out oxygen from the converting electrode 26 thereby to reduce $NO_2$ into NO. The level of the applied voltage is selected according to the drive temperature, the oxygen concentration in the atmospheric air, and the converting electrode material employed.

Figure 9:
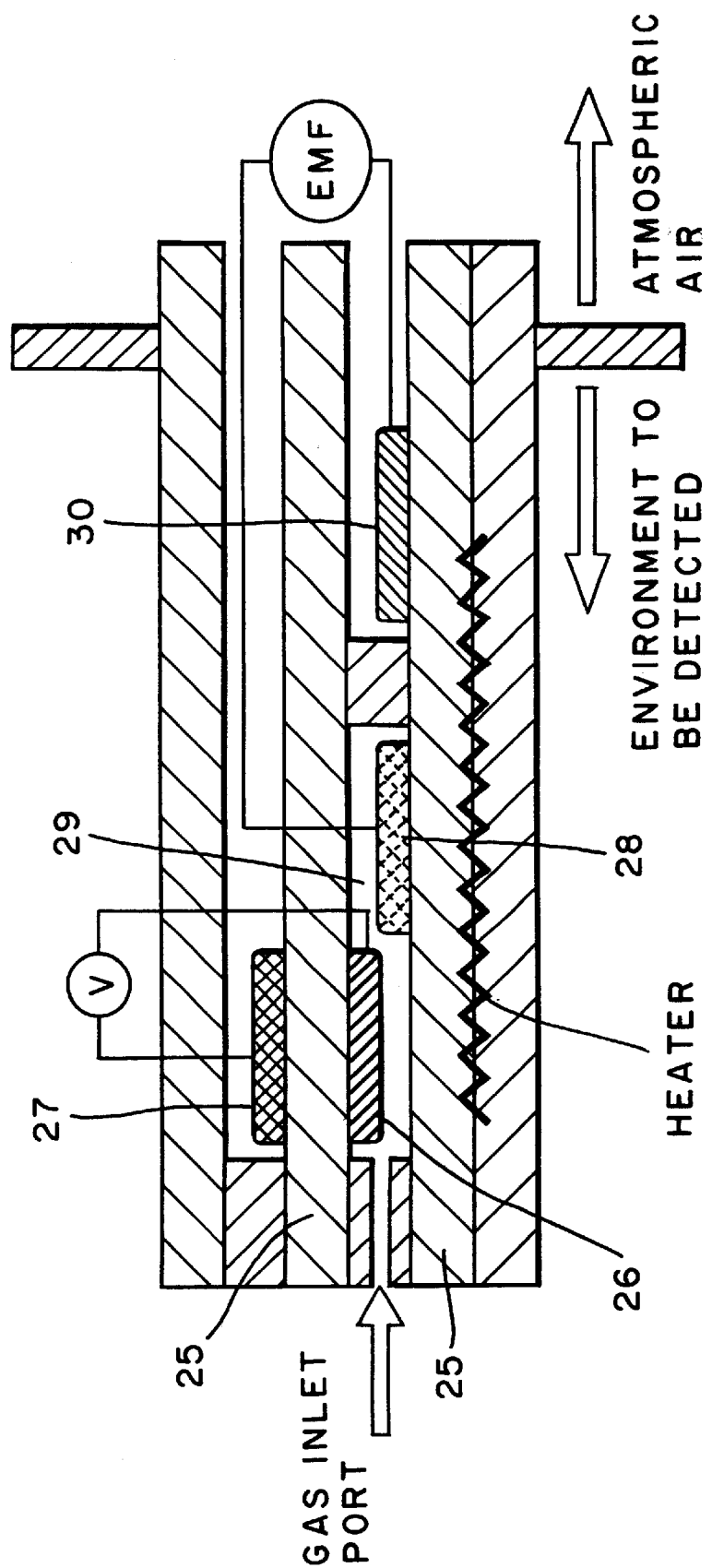
FIG. 9 is a schematic section showing a laminated type total nitrogen oxide sensor of the invention.

FIG. 9 shows one example of a laminated type total nitrogen oxide sensor which is constructed by combining the nitrogen oxide converting device having the construction shown in FIG. 8 and a mixed potential type nitrogen oxide sensor.

In the laminated type total nitrogen oxide sensor, a detecting electrode 28 of an electromotive type or mixed potential type sensor and the converting electrode 26 of the converting device are counted in a gas chamber 29, and the NO and $NO_2$ mixed gases in the gas to be detected is converted into a single gas of NO or $NO_2$ by using the converting device so that the total nitrogen oxide concentration is measured by the electromotive force type or mixed potential type sensor.

The electromotive force or mixed potential type sensor is constructed by forming the nitrogen oxide detecting electrode 28 of platinum and rhodium and a platinum reference electrode 30 on the stabilizing zirconia substrate 25.

The description will be made by the following detailed examples.

(Example 5)

The converting device having the construction, as shown in FIG. 8, was made by employing a green sheet of zirconia stabilized with 6 mol % of yttria, as the oxygen ion conductor. This green sheet 25 had been prepared by the doctor blade method to have a thickness of about 0.3 mm. The converting electrode 26 and the platinum counter electrode 27 were formed by applying an electrode paste by the screen printing method. The converting electrode paste was prepared by adding the 6 mol % yttria stabilized zirconia fine powder to either a mixture of fine platinum powder and fine ruthenium (Ru) powder or a fine alloy powder of platinum and ruthenium, and by adding a predetermined amount of organic binder or organic solvent to the mixture or the fine powder and kneading them. The amount of ruthenium was at 0.1 to 20 wt % to the total amount of platinum and ruthenium.

The paste for the platinum counter electrode 27 was prepared by adding a predetermined amount of organic binder or solvent to fine powder of platinum and fine powder of stabilizing zirconia and by kneading them. The sample in the prepared green sheet state was baked at 1,400° C. to attach platinum lead wires to the electrodes. The baked electrode area was 2 mm×3.5 mm.

The oxidizing ability of NO was mainly evaluated as the nitrogen oxide converting ability. The converting device was heated to 600° C., and a voltage of 0.1 to 1.0 V was applied to the converting electrode 26 with respect to the platinum counter electrode 27. The gas, in which 4% of oxygen was added to 300 ppm of NO diluted with nitrogen, and 4% of oxygen gas diluted with nitrogen were individually fed to the converting electrodes. The current to flow through the converting device was measured, and the current difference was defined as the NO oxidizing current and evaluated as the NO oxidizing ability of the converting electrodes.

Figure 10:
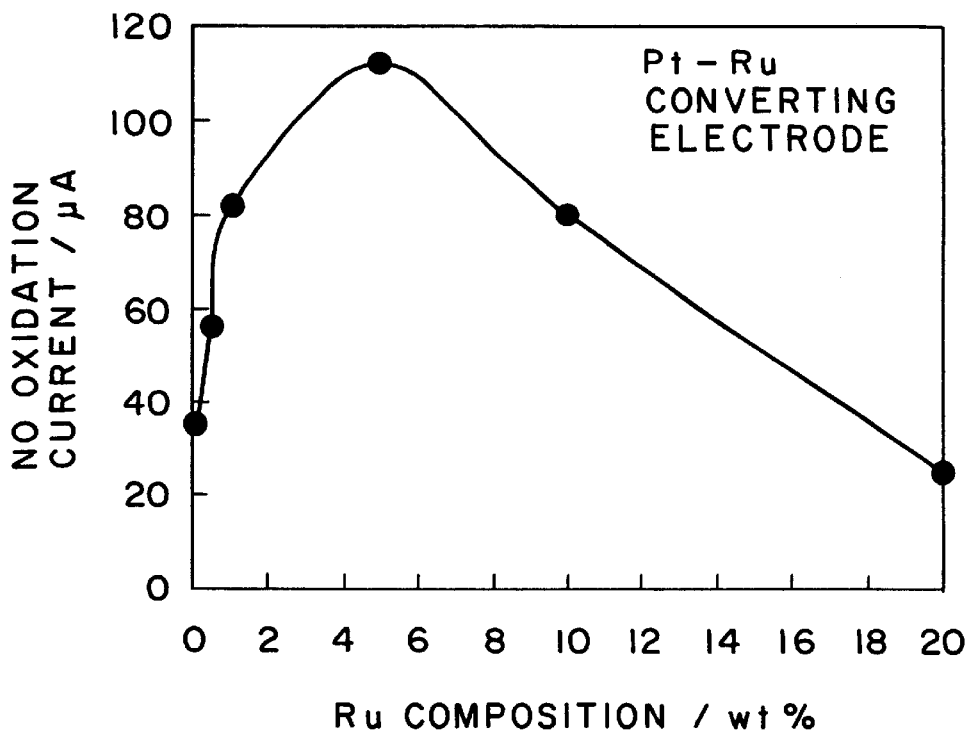
FIG. 10 is a graph illustrating a Ru composition dependency of a NO oxidation current in a Pt—Ru converting electrode.

FIG. 10 plots the dependency of the NO oxidation current on the Ru composition in the converting device to which a voltage of 0.5 V was applied. In the converting electrode 26 composed of platinum and ruthenium (Ru), the NO oxidation current was obtained for the amount of ruthenium within a range of 0.1 to 20 wt % with respect to the total weight of platinum and ruthenium. The NO oxidation current exhibited a high level especially in the vicinity of 5 wt % and was higher by 20% or more than that of the converting electrode of the prior art composed of platinum and rhodium.

(Example 6)

Figure 11:
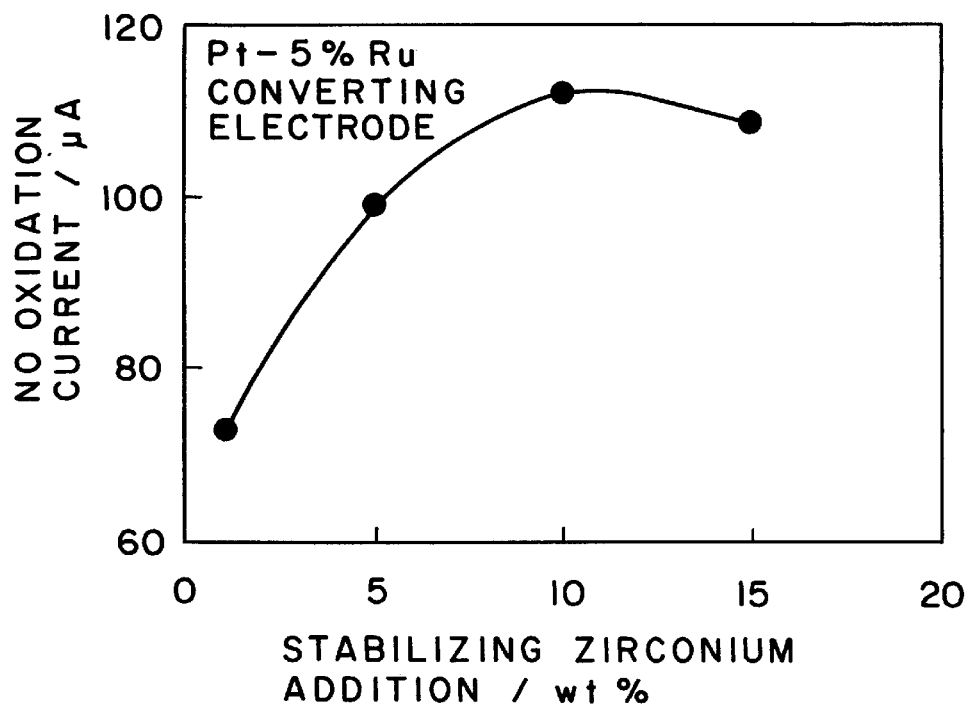
FIG. 11 is a graph illustrating a stabilizing zirconia composition dependency of the NO oxidation current in the Pt—Ru converting electrode.

The nitrogen oxide converting device was made as in Example 5. In the converting electrode 26 made of platinum and ruthenium, for a constant composition of ruthenium at 5 wt %, the amount of addition of 6 mol % yttria stabilized zirconia having a particle size of 0.1 to 5.0 μm was changed to 1 wt %, 5 wt %, 10 wt %, 15 wt % and 20 wt %. FIG. 11 plots a relation between the NO oxidation current and the amount of addition of stabilized zirconia at an applied voltage of 0.5 V and at a temperature of 600° C. For the more addition of zirconia, the particle growth of precious metal is suppressed the more when baked, so that the finer electrode is obtained.

By adding the stabilized zirconia, on the other hand, the three-phase interface is increased to raise the activity of the electrodes. For the excessive addition of zirconia, however, the electric conduction between each precious metal particle cannot be sufficiently obtained and the ability of conversion of the electrode is decreased. It is found that the invention exhibits the highest NO oxidation current when about 10 wt % of zirconia is added.

However, the amount of addition of zirconia has to be adjusted more or less according to the particle diameter of the zirconia powder. It is also found that the electrode film had no electric conduction when 20 wt % of stabilizing zirconia was added.

(Example 7)

Figure 12:
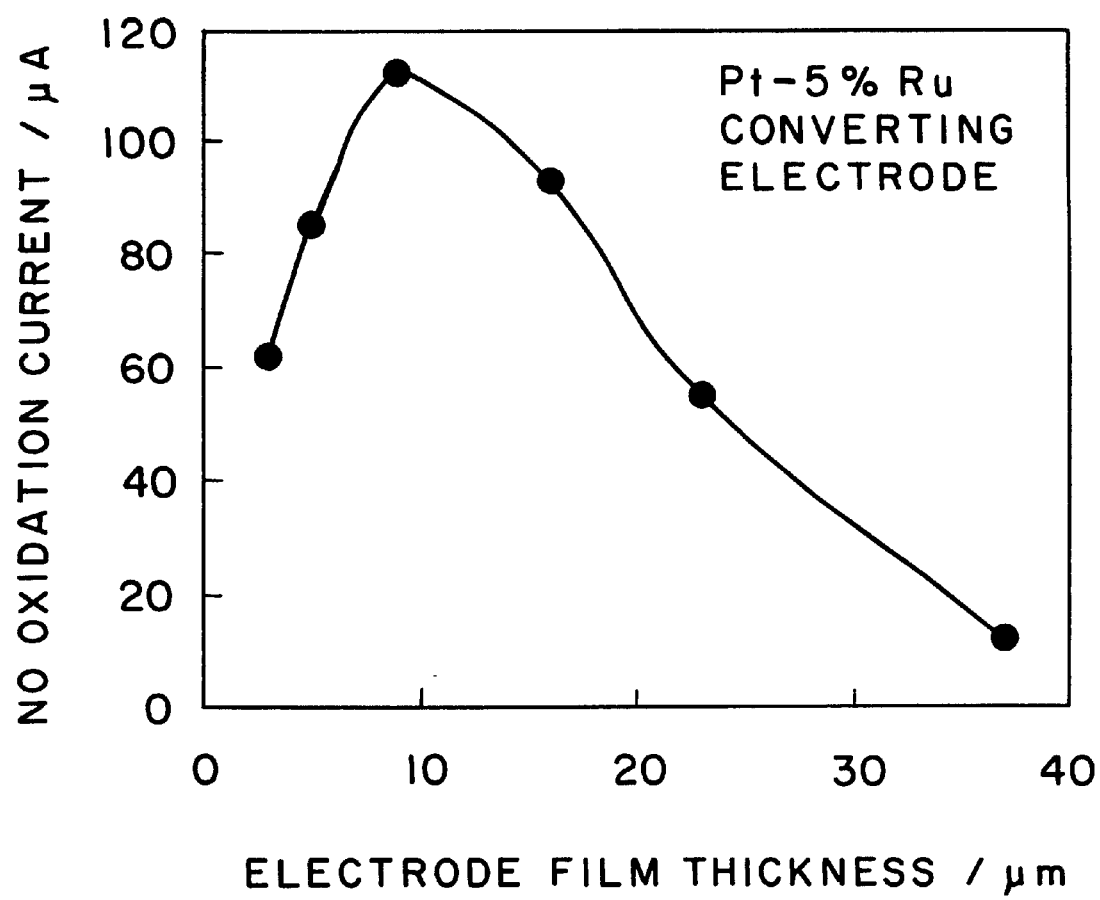
FIG. 12 is a graph illustrating an electrode film thickness dependency of the NO oxidation current in the Pt—Ru converting electrode.

The dependency of the NO oxidation current of the nitrogen oxide converting device, as made as in Example 5, upon the converting electrode film thickness was examined. The converting electrode composition was fixed at 85 wt % of platinum, 5 wt % of ruthenium and 10 wt % of 6 mol % yttria stabilized zirconia, but the electrode film thickness was changed to 3, 5, 9, 16, 23 and 37 μm. The NO oxidation current of each converting electrode at an applied voltage of 0.5 V and at a temperature of 600° C. is plotted in FIG. 12. A high NO oxidation current was obtained in the vicinity of the electrode thickness of 10 μm. As the converting electrode becomes thick, the active points become more. However, an excessively thick converting electrode will change its shape to deteriorate the migration of the gas.

(Example 8)

The nitrogen oxide converting device was made as in Example 5, but the $NO_2$ converting electrode had a composition of 82 wt % of platinum, 5 wt % of ruthenium, 3 wt % of third element and 10 wt % of 6 mol % yttria stabilized zirconia. One kind of rhodium, iridium, palladium, gold and silver was added as a third element. The precious metal powder of the three components employed was a powder mixture of individual precious metals or a fine alloy powder.

Figure 13:
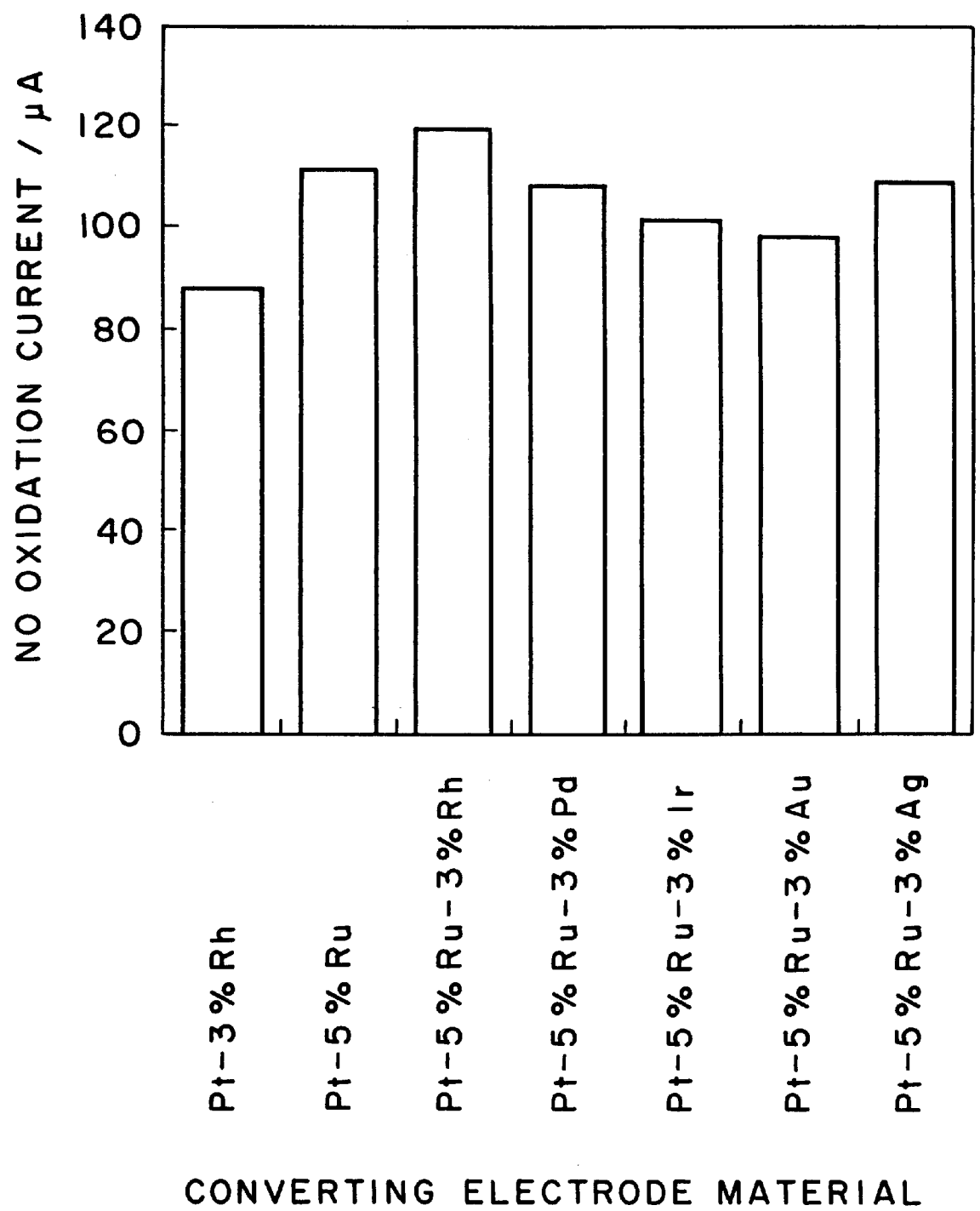
FIG. 13 is a graph illustrating relations between NO oxidation currents and converting electrode materials in a conversion device of the invention.

The results of the NO oxidation current, as measured under conditions similar to those of Example 5, are plotted in FIG. 13. For comparisons, there are presented in FIG. 13 the NO oxidation currents, as measured under the similar conditions, for the converting electrode of 85 wt % of platinum, 5 wt % of ruthenium and 10 wt % of 6 mol % yttria stabilized zirconia, and for a converting electrode of 87 wt % of sufficiently obtained and the ability of conversion of the electrode is decreased platinum, 3 wt % of rhodium and 10 wt % of 6 mol % yttria stabilized zirconia.

Of any of the NO converting electrodes having measured high NO oxidation currents, the converting electrode of platinum and ruthenium exhibited a higher NO oxidation current than that of the converting electrode of platinum and rhodium. It is also found that the No oxidation current was increased by adding rhodium as a third element to platinum and ruthenium.

(Example 9)

Figure 14:
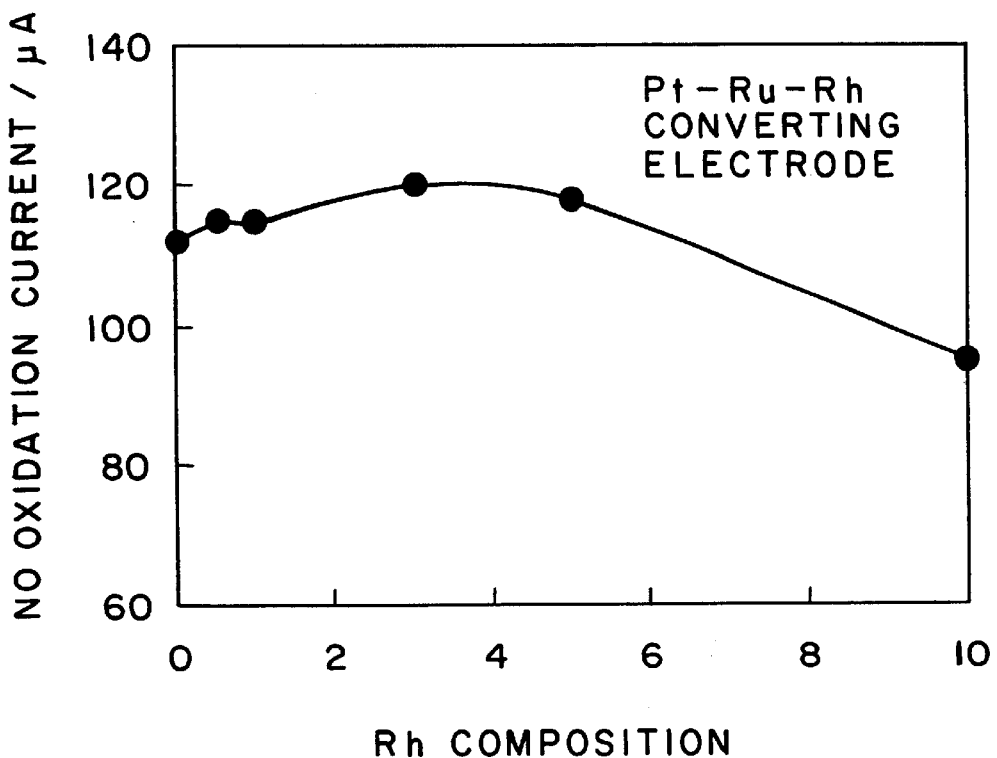
FIG. 14 is a graph illustrating a Rh composition dependency of a NO oxidation current in a Pt—Ru—Rh converting electrode.

The oxygen oxide converting device was made as in Example 8. In the converting electrode composed of platinum, ruthenium and rhodium, the amounts of additions of ruthenium and zirconia were fixed at 5 wt % and 10 wt %, respectively, and the composition of rhodium as the third element was changed to 0.5 wt %, 1 wt %, 3 wt %, 5 wt % and 10 wt %. The dependency of the NO oxidation current on rhodium at an applied voltage of 0.5 V and at a temperature of 600° C. is plotted in FIG. 14.

It is found that the NO oxidation current is remarkably reduced as the amount of addition of rhodium exceeds 5 wt %. It is also found that a high NO oxidation current is exhibited in the vicinity of the rhodium addition of 3 wt %.

(Example 10)

A laminated type total nitrogen oxide sensor having a structure shown in FIG. 9 was made by employing a green sheet of 6 mol % yttria stabilized zirconia having a thickness of about 0.3 mm. In the nitrogen oxide converting device, the converting electrode and the platinum counter electrode were formed by the screen printing method. The outputs of the sensor were compared by preparing a converting electrode of 85 wt % of platinum, 5 wt % of ruthenium and 10 wt % of 6 mol % yttria stabilized zirconia, and a converting electrode of 87 wt % of platinum, 3 wt % of rhodium and 10 wt % of 6 mol % yttria stabilized zirconia. The platinum counter electrode had a composition of 90 wt % of platinum and 10 wt % of 6 mol % yttria stabilized zirconia.

The electromotive force type or mixed potential type nitrogen oxide sensor was made like the nitrogen oxide converting device. However, the detecting electrode had a composition of 85 wt % of platinum, 5 wt% of rhodium and 10 wt % of 6 mol % yttria stabilized zirconia.

The laminated total nitrogen oxide sensor having the structure shown in FIG. 9 was made by contact-bonding the electromotive force type or mixed potential type nitrogen oxide sensor sheet, the nitrogen oxide converting device sheet, the gas chamber forming zirconia green sheet and the sheet having the heater, and by baking the bonded sheets at 1,400° C.

The potential difference between the detecting electrode and the reference electrode was measured while applying a voltage of 0.5 V to the nitrogen oxide converting device at 600° C. and feeding the sensor with the measuring gas in which 4% of oxygen and 50 to 400 ppm of NO or $NO_2$ were added to the nitrogen base. Since the potential of the reference electrode in the atmospheric air was constant at all times, the electromotive force (EMF) of the detecting electrode was measured as the output of the sensor.

Figure 15:
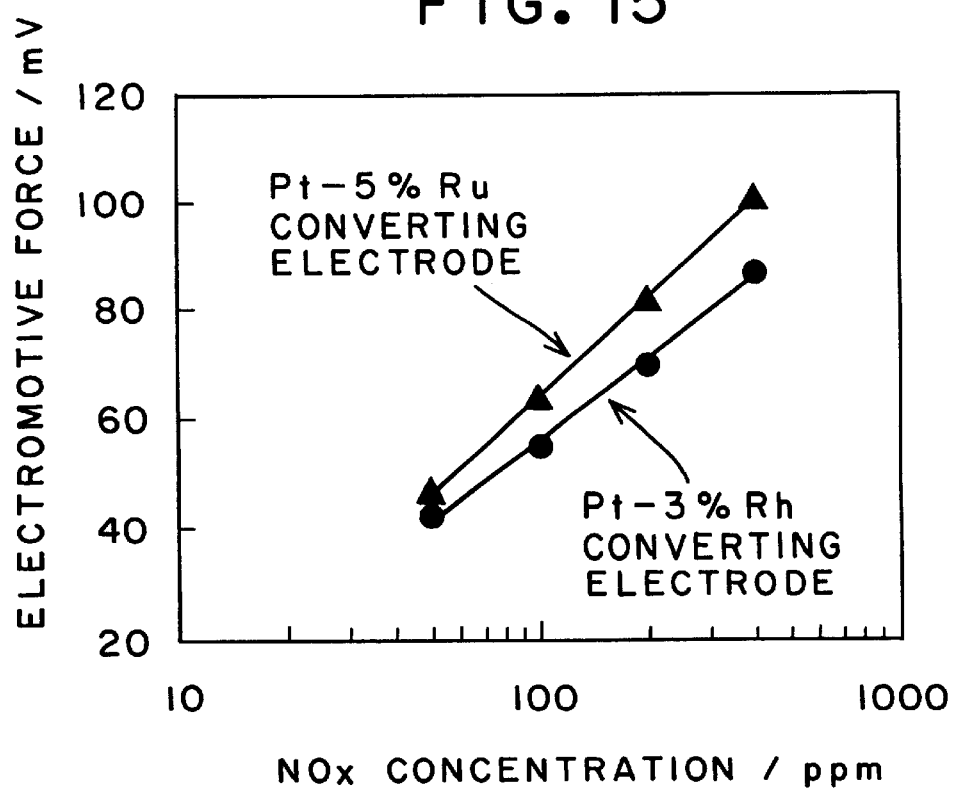
FIG. 15 is a graph illustrating the relations between the sensor outputs and the converting electrode materials in the laminated type total nitrogen oxide sensor of the invention.
Figure 16:
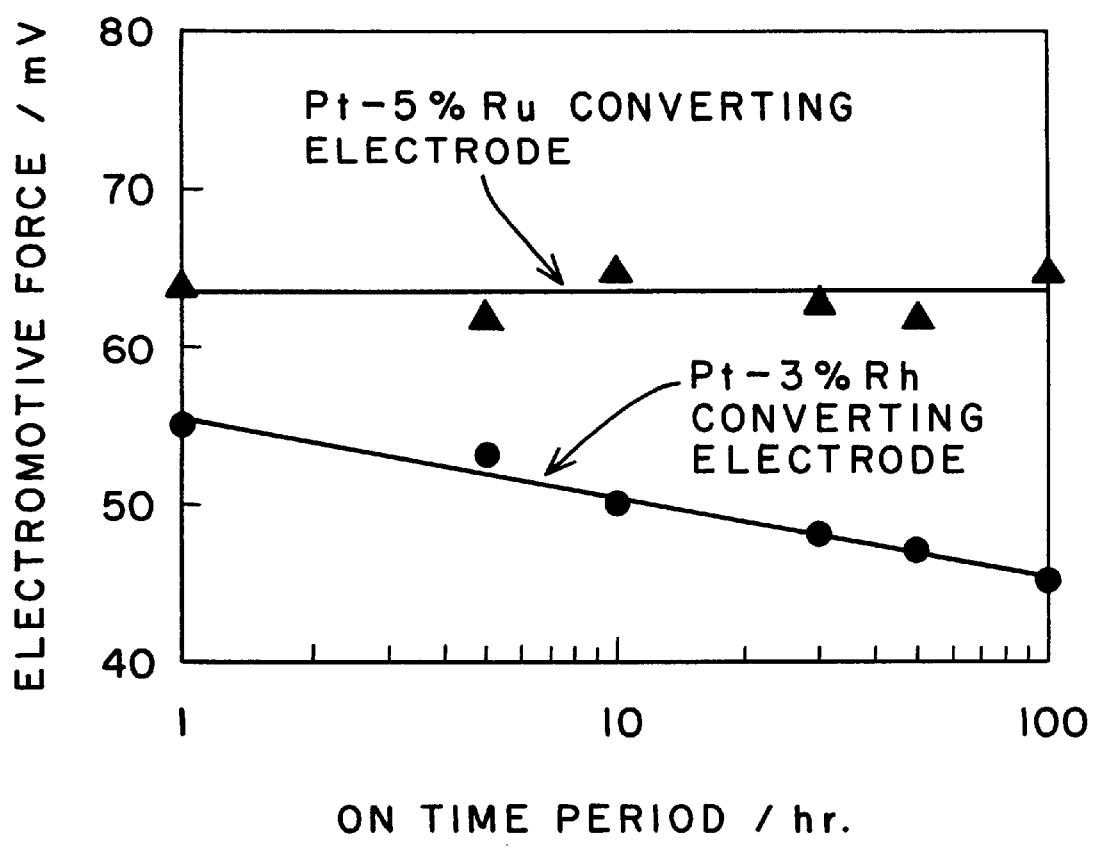
FIG. 16 is a graph illustrating the relations between stability of the sensor outputs and the converting electrode materials in the laminated type total nitrogen oxide sensor of the invention.

FIG. 15 compares the outputs of the laminated type sensors employing different converting electrode materials. It is found that the output of the sensor employing the converting electrode of platinum and ruthenium was higher than that of the sensor employing the converting electrode of platinum and rhodium. At 600° C. and at an applied voltage of 0.5 V, moreover, the relations between the outputs of the two sensors for a mixed gas of 50 ppm of NO and 50 ppm of $NO_2$ and the ON time period of applying voltage to the converting device were examined, and the results are plotted in FIG. 16. As the ON time period grows longer, the output of the sensor employing the converting electrode of platinum and rhodium grows lower.

On the other hand, it is found that the output of the sensor employing the converting electrode of platinum and ruthenium fluctuates more or less but is substantially stable. By employing the converting electrode of platinum and ruthenium, therefore, the output of the sensor is higher and stabler than that of the sensor of the prior art.

By the nitrogen oxide sensor of the invention, of the nitrogen oxide gas in the environment to be detected, NO in the mixed gases of NO and $NO_2$ is efficiently converted into $NO_2$, a nitrogen peroxide gas over $NO_2$, and their mixture gases, and adversely $NO_2$ is efficiently converted into NO so that the potential difference, as based on the total of the nitrogen oxide gas, can be detected in a high sensitivity between the detecting electrode and the counter electrode.

By employing the converting electrode which is made of platinum and ruthenium and has a higher nitrogen oxide converting ability than that of the converting electrode of platinum and rhodium, the output of the laminated type total nitrogen oxide sensor, as shown in FIG. 9, is increased so that the nitrogen oxide of a lower concentration can be detected. Since the concentration dependency of the sensor output has a large gradient, moreover, the accuracy and resolution in the concentration measurement of the nitrogen oxide can be improved. In addition, the output of the sensor is not deteriorated even the power is continuously supplied, so that a stable sensor output can be achieved.

What is claimed is:

1. A nitrogen oxide sensor comprising:
   a gas chamber communicating with an environment to be detected,
   an oxygen pumping portion mounted on a solid electrolyte body forming a wall of said chamber for sucking or discharging an oxygen gas electrochemically and including an oxygen pumping electrode in said gas chamber, said oxygen pumping electrode also serving as an NOx converting electrode and comprising an alloy of Pt and 1 to 20 wt. % of Rh;
   a NOx gas detecting portion for detecting NOx including a detecting electrode and a counter electrode mounted on a solid electrolyte body separate from that on which said oxygen pumping portion is mounted and either the detecting electrode or the detecting electrode and the counter electrode of said NOx gas detecting portion being arranged in said gas chamber so that at least said detecting electrode faces said oxygen pumping electrode serving as an NOx converting electrode, a gas inlet port for introducing a gas to be measured from said environment into said gas chamber and having a diffusion resistance such that NOx is converted in said gas chamber at a voltage of of 1.5 V or lower applied to said oxygen pumping electrode serving as an NOx converting electrode;

a heating mechanism for keeping said oxygen pumping portion and said NOx gas detecting portion within a predetermined temperature range, and means for measuring the NOx concentration on a basis of an electromotive force generated between said detecting electrode and said counter electrode.

2. A NOx sensor according to claim 1, further comprising auxiliary oxygen pumping means for controlling the oxygen concentration in said NOx gas detecting portion to a predetermined value within a range of 0.01 to 10%.

3. A NOx sensor according to claim 1, further comprising preliminary oxygen pumping means for oxidizing interference reducing gases including hydrocarbon gases or CO to non-interference gases, in which at least one electrode of said preliminary oxygen pumping means disposed in said gas chamber is arranged in a portion closer to said gas inlet port than said detecting electrode.

4. A NOx sensor according to claim 1, further comprising an oxidizing or reducing catalyzer interposed between said oxygen pumping portion and said NOx gas detecting portion for preventing the converted NOx gas from being reduced or oxidized before it reaches said detecting electrode.

5. A NOx sensor according to claim 1, further comprising a porous body interposed between said NOx converting electrode and said NOx gas detecting electrode.

6. A NOx sensor according to claim 5, wherein said porous body has an electrically high resistance.

7. A NOx sensor according to claim 1, wherein said oxygen pumping electrode serving as an NOx converting electrode comprises a mixture of said alloy and 5 to 15 wt. % of $ZrO_2$ particles having a diameter of 0.1 to 5.0 μm.

8. A nitrogen oxide sensor comprising:

a gas chamber communicating with an environment to be detected, an oxygen pumping portion mounted on a solid electrolyte body forming a wall of said chamber for sucking or discharging an oxygen gas electrochemically and including an oxygen pumping electrode in said gas chamber, said oxygen pumping electrode also serving as an NOx converting electrode and comprising an alloy of Pt and 1 to 10 wt. % of Ru;

a NOx gas detecting portion for detecting NOx including a detecting electrode and a counter electrode mounted on a solid electrolyte body separate from that on which said oxygen pumping portion is mounted and either the detecting electrode or the detecting electrode and the counter electrode of said NOx gas detecting portion being arranged in said gas chamber so that at least said detecting electrode faces said oxygen pumping electrode serving as an NOx converting electrode, a gas inlet port for introducing a gas to be measured from said environment into said gas chamber and having a diffusion resistance such that NOx is converted in said gas chamber at a voltage of of 1.5 V or lower applied to said oxygen pumping electrode serving as an NOx converting electrode;

a heating mechanism for keeping said oxygen pumping portion and said NOx gas detecting portion within a predetermined temperature range, and means for measuring the NOx concentration on a basis of an electromotive force generated between said detecting electrode and said counter electrode.

9. A NOx sensor according to claim 8, wherein said oxygen pumping electrode serving as an NOx converting electrode consists essentially of Pt, 5 wt. % of Ru, and 3 wt. % of one element selected from the group consisting of Rh, Pd, Ir, Au and Ag.

10. A NOx sensor according to claim 8, wherein said oxygen pumping electrode serving as an NOx converting electrode comprises a mixture of said alloy and 5 to 15 wt. % of $ZrO_2$ particles having a diameter of 0.1 to 5.0 μm.

* * * * *